United States Patent [19]

Szymski

[11] 4,438,921
[45] Mar. 27, 1984

[54] CALIBRATION OF LOAD INDICATOR FOR ERGOMETRIC EXERCISER

[75] Inventor: Eugene J. Szymski, Skokie, Ill.

[73] Assignee: Schwinn Bicycle Company, Chicago, Ill.

[21] Appl. No.: 271,675

[22] Filed: Jun. 8, 1981

[51] Int. Cl.³ .......................... A63B 21/00; G01L 5/28
[52] U.S. Cl. .......................................... 272/73; 73/130
[58] Field of Search ................... 272/73; 73/1 R, 1 B, 73/1 C, 1 D, 1 J, 4 R, 4 D, 121, 126, 127, 130, 73/131, 498, 862.62; 188/24.11, 24.12, 24.15, 24.14, 188/24.14, 24.16, 1.11

[56] References Cited

U.S. PATENT DOCUMENTS

| Re. 29,404 | 9/1977 | Blevens | 188/24.16 |
| 334,635 | 1/1886 | Bowen | 272/73 |
| 1,676,774 | 7/1928 | Cronk | 73/131 |
| 2,510,973 | 6/1950 | Guillemin, Jr. | 272/73 UX |
| 2,680,967 | 6/1954 | Newman | 73/862.62 X |
| 3,882,971 | 5/1975 | Peckham, Jr. | 188/24.16 |
| 3,929,209 | 12/1975 | Peckham, Jr. | 188/24.16 |
| 3,995,491 | 12/1976 | Wolfla | 272/73 X |
| 4,289,309 | 9/1981 | Hoffmann | 272/73 |
| 4,313,602 | 2/1982 | Sullivan | 272/73 |

FOREIGN PATENT DOCUMENTS

| 1961488 | 7/1970 | Fed. Rep. of Germany | 272/73 |
| 857814 | 4/1940 | France | 272/73 |
| 900660 | 10/1944 | France | 188/24.14 |
| 269020 | 10/1950 | Switzerland | 188/24.16 |
| 300943 | 11/1928 | United Kingdom | 73/130 |

Primary Examiner—Robert A. Hafer
Assistant Examiner—Arnold W. Kramer
Attorney, Agent, or Firm—McCaleb, Lucas & Brugman

[57] ABSTRACT

Method and apparatus for effecting precise adjustment of pointer on load indicator of ergometric exerciser having pedal-actuated wheel, adjustable caliper brakes engaging wheel and mounted on a pivoted frame for movement by the wheel to actuate load indicator pointer, and including introducing an adjustable biasing force against movement of pivoted frame in form of a spring and adjustable calibration screw and locknut engaging the spring, the biasing force being adjusted by hanging a weight from periphery of wheel, adjusting brakes to just prevent weight from turning wheel, manually turning wheel slightly in forward direction, allowing slight slippage of wheel past brakes, rapping side of wheel briskly adjacent brakes and noting reading of load indicator, manually rotating wheel slightly in rearward direction without brake slippage and repeating last recited step, and adjusting calibration screw in accordance with average of said readings to bring pointer to proper position.

2 Claims, 8 Drawing Figures

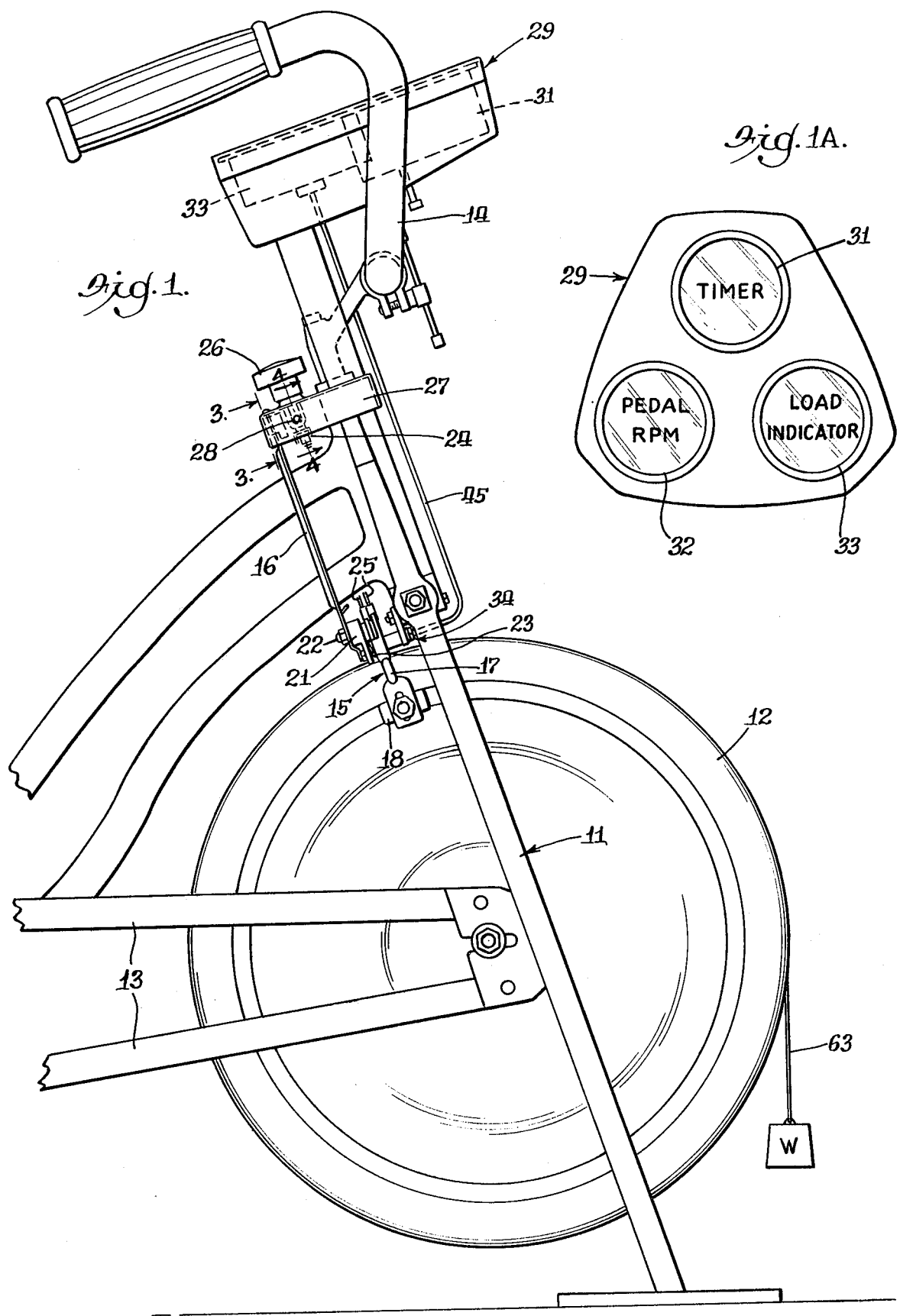

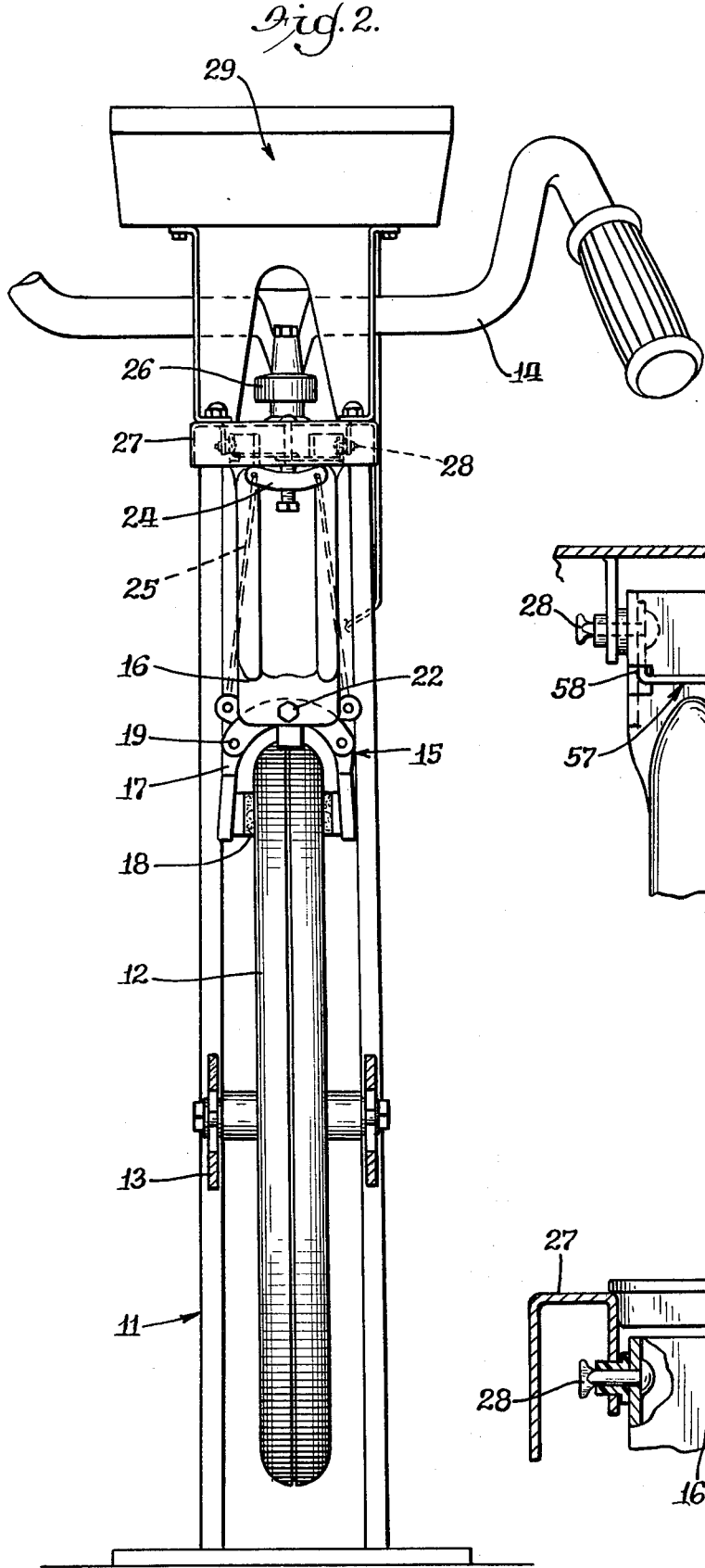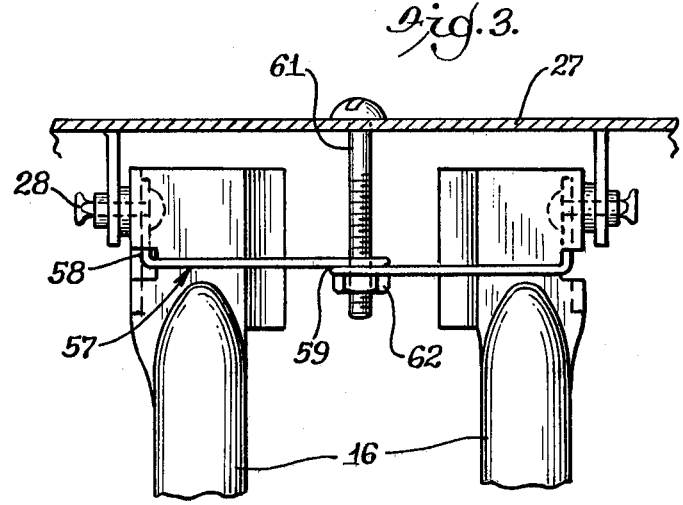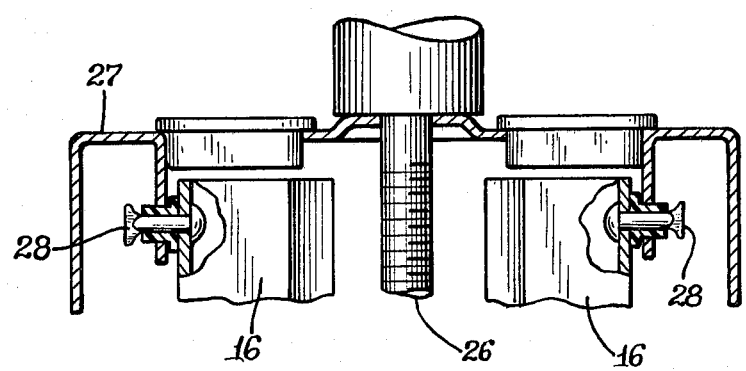

CALIBRATION OF LOAD INDICATOR FOR ERGOMETRIC EXERCISER

BACKGROUND OF THE INVENTION

1. Field of the Invention

This invention relates to bicycle-type ergometric exercisers and, more particularly, to those having a pedal-actuated wheel and adjustable brakes frictionally engaging the same to move a load indicator in accordance with the energy input by an operator in actuating the wheel.

2. Description of the Prior Art

The most pertinent prior art exerciser is that disclosed in the application for U.S. Letters Pat. Ser. No. 32,242, filed Apr. 20, 1979 and now U.S. Pat. No. 4,291,872, in which the brakes are mounted on a frame pivoted on the wheel support means for movement by the brakes to actuate transducer means to transmit movement of the frame to gauge means for indicating the energy input of an operator in pedal actuation of the wheel. Despite very careful measurements and calculations to determine the proper calibration or face dial graduations of such gauge means for cooperation with its indicating pointer to display the energy being expended at the pedals, it developed from tests made after field use that the indications of energy input to the pedals given by the gauge means did not correspond to the actual energy input to the pedals as determined by dynamometer checks. It had been planned to employ a calibration technique to determine whether any unit was properly calibrated by wrapping a chord around the periphery of the wheel with a free end supporting a ten pound weight and adjusting the brakes or resistance control to prevent the wheel from being rotated by the weight, the unit being considered to be within acceptable calibration if the pointer then indicated a load level between 6.09 and 7.01.

From those tests after field use, plotting of the load indicator settings against pedal energy input produced a slope parallel to the theoretical slope, showing the errors of the gauge indications which were felt to be attributable to failure properly to adjust for minimum friction and subsequent lowering of the friction, as in the wheel and crank bearings, due to use. This also established the inadequacy of the then planned calibration technique because it would have shown that the load indicator was in calibration at the higher settings but had a considerable error at the lower load setting.

SUMMARY OF THE INVENTION

In order to effect precise calibration of the load indicator in an ergometric exerciser having support means, a wheel rotatably mounted thereon, pedal means actuatably mounted thereon, pedal means actuatable by an operator to rotate the wheel, a frame mounted on the support means for movement relative thereto, adjustable brake means mounted on the frame for frictionally engaging the wheel and moving the frame relative to the support means in accordance with the energy input by the operator in actuating the pedal means to actuate the load indicator; biasing means providing a relatively constant biasing force is interposed between the support means and the frame, and adjustable calibration means is provided for selectively variably adjusting such biasing force. The method of this invention for effecting the desired precise adjustment of the load indicator comprises the following steps:

(1) suspending a weight by a cord from the forwardly disposed periphery of the wheel;
(2) raising the weight until it hangs freely by manually rotating the wheel backwards;
(3) adjusting the resistance control means to just prevent the weight from turning the wheel;
(4) manually rotating the wheel slightly forward, allowing slight slippage past the brake means;
(5) rapping the side of the wheel briskly several times just behind the brake means, and noting the reading of the load indicator;
(6) slightly rotating the wheel backwards, without slippage of the brake means, and repeating step 5; and
(7) adjusting the calibration means to compensate for the average readings obtained in steps 5 and 6 to effect a precise initial reading of the load indicator.

In the drawings:

FIG. 1 is a side elevation of the front portion of a bicycle-type ergometric exerciser embodying the features of the invention, with some parts omitted for the sake of clarity;

FIG. 1A is a plan view of gauge means to indicate the work rate input of an operator;

FIG. 2 is an end view, with parts in section, as seen from the left of FIG. 1;

Figure 5:
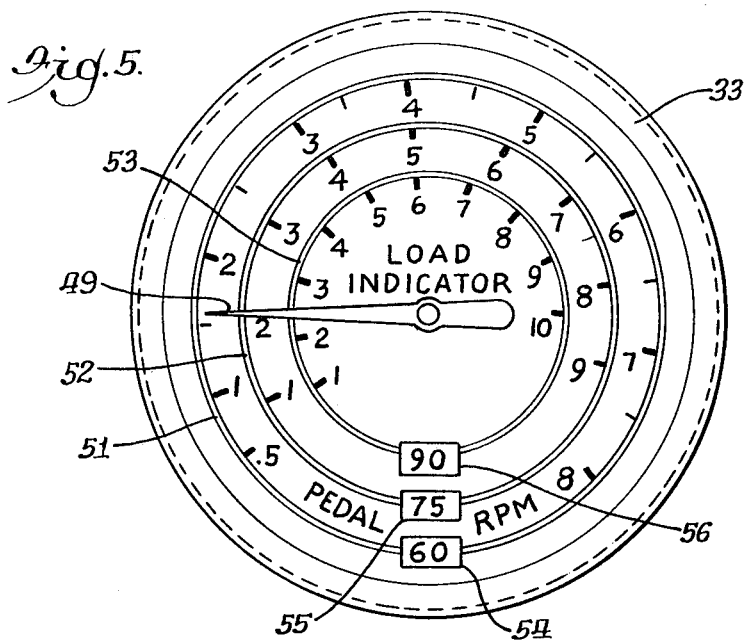
Figure 6:
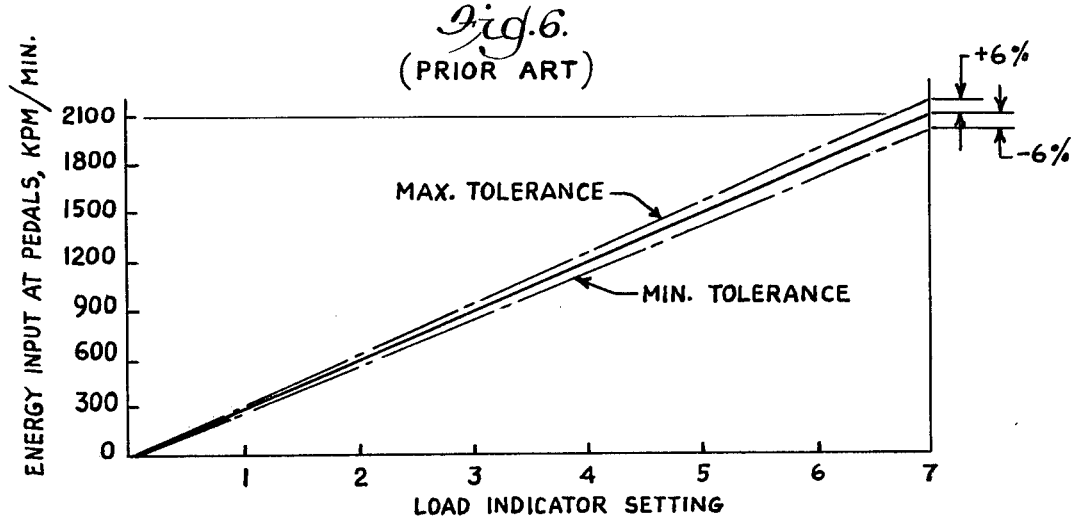
Figure 7:
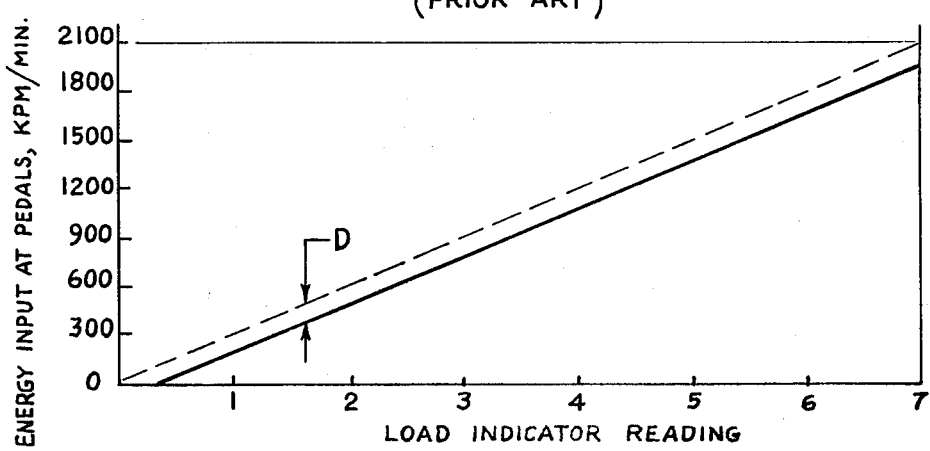

FIGS. 3 and 4 are sectional views on an enlarged scale taken substantially on the lines 3—3 and 4—4, respectively, of FIG. 1;

FIG. 5 is a detail plan view of the load indicator of FIG. 1A on an enlarged scale; and FIGS. 6 and 7 are graphic representations of load indicator settings relative to energy input.

DESCRIPTION OF THE PREFERRED EMBODIMENT

The preferred embodiment of the invention is herein illustrated as incorporated in a bicycle-type ergometric exerciser as disclosed in Ser. No. 32,242, previously identified, which includes a suitable stationary support means 11 and a wheel 12 mounted thereon for rotation in well-known manner by pedal means (not shown) actuated by an operator. Such pedal means could be like that shown in U.S. Pat. No. 3,995,491 as including a pedal-actuated drive sprocket and a chain engaging the same and extending within the usual guard, herein designated by reference numeral 13, for rotating a driven sprocket secured to the wheel. The exerciser also includes a suitable handlebar 14 adjustably mounted on the support means 11 for the convenience of the exercising operator.

Adjustable brake means, indicated generally by reference numeral 15, is supported adjacent the lower end of a frame or pivot arm 16 and comprises a pair of caliper brake arms 17 with friction pads 18 on their lower ends engageable with opposite sides of a rim portion of wheel 12. Similar brake arms and friction pads or brake blocks are disclosed in U.S. Pat. No. 3,305,048. The brake arms 17 are pivotally supported at 19 on a stirrup 21 secured adjacent its upper end at 22 to the lower portion of the frame 16, are lightly urged by a spring 23 (FIG. 1) away from each other and the wheel rim, and are adjustably moved and held in frictional engagement with the wheel by a threaded yoke 24 (FIG. 2) interconnected, respectively, with the upper ends of the two brake arms 17 by rods 25. The threaded yoke 24 is supported and moved vertically by a brake pressure adjusting screw 26 suitably supported in turn by a bracket 27 mounted on the support means 11. Thus, lifting of the threaded yoke 24 in response to rotation of the adjusting screw 26 will frictionally engage the caliper brake pads 18 with the opposite sides of the rim portion of wheel 12.

The upper ends of the frame or pivot arm 16 (FIGS. 1 and 2) are pivotally supported at 28 in the bracket 27. Consequently, if the wheel 12 is being rotated by the operator in a clockwise direction, as viewed in FIG. 1, and the caliper brake means 15 has been adjusted by screw 26 to frictionally engage the rim of wheel 12, the lower end of the frame or arm 16 and the stirrup 21 thereon will be moved to the right or forwardly in accordance with the work rate input being exerted by the operator.

Instrument panel means, indicated generally by reference numeral 29, is mounted on the support means 11 in any suitable manner at a position centrally of the handlebar 14 to conveniently indicate to the operator such work rate input resulting from the pressure being maintained against the rim of the wheel 12 by the brake means 15 as the wheel is rotated by the operator. That instrument panel or gauge means preferably includes a timer 31 of any desired type (FIG. 1A), a wheel or pedal RMP indicator 32 operable in well-known manner by the pedals or wheel, and an hydraulically operated load indicator 33 to show, as in kilogram-meters per minute, or foot-pounds per minute, the energy being expended by the operator.

The indicator 33 is actuated by hydraulic transducer means indicated generally by reference numeral 34 in FIG. 1 which in the preferred embodiment includes an hydraulic load cell, as fully disclosed in said Ser. No. 32,242, operable by forward movement of the lower end of the frame or pivot arm 16, as previously noted, to exert pressure against a suitable viscous fluid therein and in the gauge 33 and a tube 45 interconnecting the transducer 34 and the gauge or indicator 33.

The reference numerals used so far herein are the same as in Ser. No. 32,242 to indicate similar parts, while those hereinafter employed identify additional means comprising the preferred embodiment of the instant invention for effecting precise calibration of the load indicator 33.

As illustrated in FIG. 5, the load indicator 33 of the gauge means comprises a pointer 49 movable clockwise from a normal at rest position in response to forward movement of the lower end of the frame or pivot arm 16 acting on the hydraulic transducer means 34, and cooperating with suitable numerals on concentric indicator bands 51, 52 and 53 corresponding, respectively, with different speeds of rotation of the wheel 12 and the pedal means actuating it, being shown as 60, 75 and 90 pedal RPM, it being understood that the operator uses the indicator band that corresponds to the reading of the pedal RPM indicator 32. To facilitate such selective use of the proper indicator band, those bands 51, 52 and 53 and their associated numerals may be colored green, yellow and red, respectively, with the same colors being used as backgrounds for pedal RPM numerals 54, 55 and 56 corresponding thereto.

As previously noted herein, the indications of energy input to the pedals given by such gauge means 33 of the exerciser of Ser. No. 32,242 were found, after field use, not to be the same as were determined by dynamometer tests. In the development of the face dial graduations illustrated in FIG. 5, the relationship between the load indicator reading or setting and the energy input into the pedals in kilogram-meters per minute was illustrated in the graph of FIG. 6, including the maximum and minimum permissible tolerances. FIG. 7 illustrates a similar graph with the theoretical slope shown by a broken line and the actual slope by a solid line determined by the readings of the load indicator 33 after the field use described. It is of interest to note that these two lines are parallel with the actual slope spaced below the theoretical slope a distance D. This illustrates the problem presented in correcting the exerciser to give accurate load indicator readings.

The present invention solves this problem by introducing a readily adjustable biasing force, preferably between the support 11 and the pivoted frame 16, for effecting precise adjustment of the pointer 49 of the load indicator 33. In the preferred embodiment herein illustrated, this biasing force is provided by a low spring rate spring indicated generally by reference numeral 57 having laterally extending legs (FIG. 3) disposed rearwardly of the upper ends of the arms of the frame 16 and terminating in forwardly and upwardly extending end portions 58 engaging under the forwardly extending pivoted portions at the upper ends of frame 16. The central portion of the spring 57 is formed as a coil 59 receiving and surrounding the shank of an adjustable calibration screw 61 extending downwardly through a suitable aperture in the bracket 27, and a locknut 62 is mounted on the screw 61 for engagement with the under side of the central coil 59 of spring 57.

The spring 57 thus is anchored at its central portion at the coil 59 against downward movement relative to the bracket 27 and support 11 by the locknut 62 on the screw 61. Forward movement of the lower portion of the pivoted frame 16, in response to rotation of the wheel 12 when the brake means 15 is engaged therewith, is resisted by the spring 57 by virtue of the lifting force of its ends 58 upon the forwardly extending pivoted portions of the frame. Such resilient force by the spring 57 against forward movement of the lower end of frame 16 is relatively constant but may be selectively modified or varied by adjustment of the locknut 62 on the screw 61 of this calibration means. It will be understood that adjustment of the locknut 62 may best be effected by holding it with a suitable wrench while rotating the screw 61, as by means of a screw driver, clockwise rotation of the screw, as viewed from above, thus raising the locknut to accordingly increase the effective resilient force of spring 57 against forward movement of the lower end of frame 16.

This adjustable biasing means comprising spring 57 and the screw 61 and locknut 62 are employed as a calibration device or means for effecting a precise initial setting or reading of the load indicator 33 in the following manner. As illustrated in FIG. 1, a cord 63 is secured in any suitable manner to the forwardly disposed periphery of the exerciser wheel 12 with a weight W attached to its lower end. When the weight W is so suspended and hangs freely, the pointer 49 of the load indicator 33 should be positioned precisely at load setting 1 of the outer indicator band 51 if the resistance control means has been adjusted by means of the screw 26 to just prevent the weight from rotating the wheel. In the specific exerciser herein disclosed, that will result with a weight of 670 grams. If the pointer of the load indicator does not give that reading precisely, it may be brought to the proper position by adjusting the calibration screw 61 and locknut 62 as previously described until it gives the desired precise initial reading. It will be understood that if the pointer reading is greater than 1, the calibration screw 61 should be turned clockwise, as seen from above, and that it should be turned counterclockwise if the reading is less than 1.

The method of the instant invention for performing such calibration of the load indicator preferably includes the following steps:

(1) suspending weight W by means of cord 63 from the forwardly disposed periphery of wheel 12;
(2) raising the weight, until the same hangs freely, by manually rotating the wheel backwards;
(3) adjusting the resistance control means 26 to just prevent the weight from turning the wheel;
(4) manually rotating the wheel slightly forward, allowing approximately one-half inch slippage of the wheel past the brake means;
(5) rapping the side of the wheel briskly several times just behind the brake means, as with the handle of a screwdriver, and noting the reading of the pointer 49 of load indicator 33;
(6) slightly rotating the wheel backwards, without slippage of the brake means, and repeating step 5;
(7) adjusting the calibration screw 61 clockwise if the average reading of steps 5 and 6 is greater than the initial scale index 1, and counterclockwise if the average reading of steps 5 and 6 is less than said 1 on the scale index; and
(8) repeating steps 4–7 until the pointer 49 coincides precisely with said 1 on the scale index.

It is thought that the invention and many of its attendant advantages will be understood from the foregoing description, and it will be apparent that various changes may be made in the form, construction and arrangement of the parts and in the sequence of the method steps without departing from the spirit of the invention or sacrificing all of its material advantages, the form hereinbefore described and shown in the drawings being merely a preferred embodiment thereof.

The embodiments of the invention in which an exclusive property or privilege is claimed are defined as follows:

1. The method of calibration for effecting precise adjustment of a load indicator in an ergometric exerciser having support means for said load indicator, a pedal-actuated wheel freely rotatably mounted on said support means, brake means mounted on a frame resiliently biased on said support means for variable frictional engagement with said wheel for movement on said frame by forward rotation of the wheel to actuate said load indicator, including adjustable resistance control means for frictionally engaging said brake means with said wheel, and adjustable calibration means interposed between said frame and said support means; comprising the following steps:

(1) suspending a weight by a cord from the forwardly disposed periphery of said wheel;
(2) raising said weight until the same hangs freely by manually rotating said wheel backwards;
(3) adjusting said resistance control means to just prevent said weight from turning said wheel;
(4) manually rotating said wheel slightly forward, allowing slight slippage past said brake means;
(5) rapping the side of said wheel briskly several times just behind said brake means, as with the handle of a screwdriver, and noting the reading of said load indicator;
(6) slightly rotating said wheel backwards, without slippage of said brake means, and repeating step 5; and
(7) adjusting said calibration means against the resilient biasing of the frame to compensate for the average readings obtained in steps 5 and 6 to effect a precise initial setting of said indicator.

2. The method of calibration for effecting precise adjustment of the indicator pointer of a load indicator relative to the initial scale index thereof in an ergometric exerciser having support means for said load indicator, a pedal-actuated wheel freely rotatably mounted on said support means, brake means mounted on a frame resiliently biased on said support means for variable frictional engagement with said wheel for movement of said frame by forward rotation of the wheel to actuate said load indicator, including adjustable resistance control means for frictionally engaging said brake means with said wheel, and adjustable calibration means interposed between said frame and said support means, including a calibration screw, comprising the following steps:

(1) suspending a weight by a cord from the forwardly disposed periphery of said wheel;
(2) raising said weight until the same hangs freely by manually rotating said wheel backwards;
(3) adjusting said resistance control means to just prevent said weight from turning said wheel;
(4) manually rotating said wheel slightly forward, allowing slight slippage past said brake means;
(5) rapping the side of said wheel briskly several times just behind said brake means, as with the handle of a screwdriver, and noting the reading of said load indicator;
(6) slightly rotating said wheel backwards, without slippage of said brake means, and repeating step 5;
(7) adjusting said calibration screw clockwise against the resilient biasing of the frame if the average reading of steps 5 and 6 is greater than the initial scale index 1, and counterclockwise if the average reading of steps 5 and 6 is less than said 1 on the scale index; and
(8) repeating steps 4–7 until said pointer coincides precisely with said 1 on said scale index.

* * * * *

UNITED STATES PATENT AND TRADEMARK OFFICE
CERTIFICATE OF CORRECTION

PATENT NO. : 4,438,921
DATED : March 27, 1984
INVENTOR(S) : Eugene J. Szymski

It is certified that error appears in the above—identified patent and that said Letters Patent is hereby corrected as shown below:

In the heading, item [73], "Schwinn Bicycle Company, Chicago, Ill." should be --Excelsior Fitness Equipment Co., Northbrook, Illinois --.

Signed and Sealed this

Eighteenth Day of September 1984

[SEAL]

Attest:

GERALD J. MOSSINGHOFF

Attesting Officer

Commissioner of Patents and Trademarks